United States Patent [19]
Schall et al.

[11] Patent Number: 5,880,964
[45] Date of Patent: Mar. 9, 1999

[54] METHOD FOR FABRICATING A COSMETIC COVER FOR A PROSTHETIC LIMB

[75] Inventors: Scott R. Schall, Englewood; Tracy C. Slemker, Clayton, both of Ohio

[73] Assignee: Prosthetic Design, Inc., Clayton, Ohio

[21] Appl. No.: 792,097

[22] Filed: Jan. 31, 1997

[51] Int. Cl.$^6$ .............................. G06F 19/00; G06G 7/64; G06G 7/66
[52] U.S. Cl. ................................ 364/474.01; 364/474.02; 364/474.16; 364/474.24; 623/27; 623/33
[58] Field of Search .................... 364/474.24, 474.01, 364/474.02, 474.03, 474.05, 474.14, 474.16, 191; 250/227.11, 560, 231.1; 425/2, 142, 164, 174.4; 623/901, 27, 33, 16, 49

[56] References Cited

U.S. PATENT DOCUMENTS

| | | | |
|---|---|---|---|
| 5,133,777 | 7/1992 | Arbogast et al. | 623/38 |
| 5,252,822 | 10/1993 | Firth | 250/227.11 |
| 5,360,446 | 11/1994 | Kennedy | 623/16 |
| 5,376,127 | 12/1994 | Swanson | 623/27 |
| 5,376,129 | 12/1994 | Faulkner et al. | 623/33 |
| 5,432,703 | 7/1995 | Clynch et al. | 364/474.05 |
| 5,539,649 | 7/1996 | Walsh et al. | 364/474.05 |
| 5,593,456 | 1/1997 | Merlette | 623/49 |
| 5,662,715 | 9/1997 | Slemker | 623/36 |
| 5,718,925 | 2/1998 | Kristinsson et al. | 425/2 |

FOREIGN PATENT DOCUMENTS

| | | | |
|---|---|---|---|
| 2087727 | 6/1982 | United Kingdom | A61F 1/04 |

*Primary Examiner*—Reba I. Elmore
*Assistant Examiner*—Ramesh Patel
*Attorney, Agent, or Firm*—Thompson Hine & Flory LLP

[57] ABSTRACT

A system and method for fabricating a cosmetic cover for a prosthetic limb comprises the steps of: fitting and aligning a prosthetic limb to a wearer's residual limb; collecting orientational and positional data from adjustment points between the various endoskeletal and/or socket components of the residual limb; transmitting the orientational data to a CAD system that has access to the socket and endoskeletal component dimensions; using the CAD system to calculate inner surface dimensions for a cosmetic cover to be worn over the prosthetic limb according to the socket and endoskeletal component dimensions and according to the orientational and positional data; and downloading the inner surface dimensions from the CAD system to a CNC milling machine, which is adapted to carve the inner surface of a cosmetic cover from a carving blank using the calculated inner surface dimensions. Preferably, the system and method also includes the steps of gathering sound-side dimensions of the opposing sound limb and transmitting the sound side dimensions to the CAD system; using the CAD system to calculate outer surface dimensions for the cosmetic cover that is a "mirror image" of the sound limb; and downloading the outer surface dimensions from the CAD system to the milling machine, which is adapted to carve the outer surface of the cosmetic cover from the carving blank using the outer surface dimensions. the data gathering and calculating steps are 4512 performed using the a digitizing tool integrated into the CAD tool.

20 Claims, 5 Drawing Sheets

FIG. 8

METHOD FOR FABRICATING A COSMETIC COVER FOR A PROSTHETIC LIMB

BACKGROUND

The present invention involves a system and method for fabricating a prosthetic limb cosmetic cover, and more particularly to a system and method for substantially completely automating the process of fabricating the cosmetic cover.

A prosthesis is often used to replace an amputated portion of the limb and to help restore the amputees ability to use that limb. A prosthesis for a lower extremity amputation will often include artificial foot and ankle components coupled to an upright assembly, which is in turn coupled to a custom-fitted socket assembly. If the amputation is an above the knee, the upright assembly will often include an artificial knee joint.

Often times, a cosmetic cover is fabricated to cover the endoskeletal components of the prosthetic limb described above to simulate the outward appearance of a "sound" limb.

Typically a cosmetic cover is fabricated by, first, taking circumferential measurements of the sound limb, typically in increments of 1"–2", along the length of the sound limb which is representative of the entire length of the prosthesis. Other Circumferential measurements are also taken of the prosthesis in a similar manner. Based upon these measurements, a commercially available tubular cosmetic cover blank is selected. The length of the cover blank is adjusted to the desirable length of the finished cosmetic cover. The inner surface (the hollow bore) of the tubular cosmetic cover blank is manually (or semi-manually) carved such that it will fit intimately over the outer surfaces of the prosthesis, and in particular, the prosthetic socket. The cover is typically stretched over the prosthetic socket, to some degree, which increases the outer circumference of the cover. After stretching over the prosthetic socket, the cover is typically bonded to the outer surface of the prosthetic socket.

Once the bonding agent has cured, the outer surface of the cosmetic cover is then manually sanded, ground or carved to obtain the desirable incremental circumferences of the sound limb. This step requires skill and experience for efficient fabrication of a desirable or acceptable cosmesis. Next, the cosmetic cover is smoothed and finished. Finishing can involve stretching layers of nylon stockinettes over the cosmetic cover and bonding them proximally to the cover, or can involve the application of a spray finish to match the pigment of the sound limb.

As is evident by the above summary, a significant amount of trial-and-error is typically required in fabricating the cosmetic cover from the tubular cosmetic cover blank. For example, the inner surfaces of the cosmetic cover are typically carved without consideration of any adjustments that may need to be made to the socket and/or endoskeletal components of the prosthetic limb. Thus, after the socket has been created and the prosthetic limb is assembled with the endoskeletal components and then fitted, adjusted and aligned on the amputee, the cosmetic cover will, at first, often not fit properly to the aligned and fitted prosthetic limb; requiring further modifications to, or a complete refabrication of, the cosmetic cover. With transfemoral (above the knee) amputees, this first cosmetic cover will often cause undesirable resistance to flexion and extension in the prosthetic limb, requiring further adjustment to, or a complete refabrication of, the cosmetic cover.

Furthermore, present cosmetic covers are fabricated out of a single-piece tubular cover blank (some manufacturers offer "discontinuous" covers having separate thigh and calf sections; however, each section remains a single piece). A disadvantage with the single-piece cosmetic covers, is that if access to the endoskeletal components is needed after the cosmetic cover has been mounted over the prosthetic limb (i.e., to make adjustments to the endoskeletal components), the cosmetic cover usually has to be cut or pulled down which will typically cause damage to the cover, and will sometimes require the entire cover to be refabricated. Also, because the cover is typically stretched over the prosthesis, circumferential tension will often cause small cuts in the cover to progress into large splits or tears.

Accordingly, a need exists for a system and method to precisely represent the prosthetic socket, limb, endoskeletal components and alignment of these items such that a cosmetic cover can be precisely milled based upon these characteristics; a need exists for a system that substantially automates the fabrication process of the cosmetic covers and that is sufficiently precise; and a need exists for a cosmetic cover that is easily fabricated and is also easily donned and removed from the prosthetic limb.

SUMMARY

The present invention provides a system and method for fabricating a cosmetic cover for a prosthetic limb comprising the steps of: (a) fitting and aligning a prosthetic limb to a wearer's residual limb; (b) collecting orientational and positional data from adjustment points between the various endoskeletal and/or socket components of the residual limb; (c) transmitting the orientational data to a CAD system that has access to the socket and endoskeletal component dimensions; (d) using the CAD system to calculate inner surface dimensions for a cosmetic cover to be worn or fastened over the prosthetic limb according to the socket and endoskeletal component dimensions and according to the orientational and positional data; and (e) downloading the inner surface dimensions from the CAD system to a computer-controlled milling machine, which is adapted to carve the inner surface of a cosmetic cover from a carving blank using the calculated inner surface dimensions.

Preferably, the system and method also includes the following steps: (f) gathering sound-side dimensions of the opposing sound limb and transmitting the sound side dimensions to the CAD system; (g) using the CAD system to calculate outer surface dimensions for the cosmetic cover that is a "mirror image" of the sound limb; and (h) downloading the outer surface dimensions from the CAD system to the milling machine, which is adapted to carve the outer surface of the cosmetic cover from the carving blank using the outer surface dimensions.

Preferably, the data gathering and calculating steps are performed using the CAD tool, which includes: (i) a memory for storing the various prosthetic limb socket and endoskeletal component dimensions; (ii) a digitizing tool for collecting the orientational and positional data of the fitted and aligned prosthetic limb components; (iii) a memory containing a software program for calculating the inner surface dimensions for the cosmetic cover based upon the prosthetic limb socket and endoskeletal component dimensions and the orientational and positional data; and (iv) a processing circuit, having access to the prosthetic limb socket and endoskeletal component dimensions and to the orientational and positional data, for executing the software program.

Preferably, the cosmetic cover is carved from a two-piece carving blank that includes two longitudinally mating portions, each portion having a substantially flat inner surface and a substantially curved or dome shaped outer surface. The two flat surfaces are adapted to mate with each other to form a substantially longitudinal cast having a substantially elliptical cross-sectional shape. Each of the two carving blank portions are separately carved in the milling machine based upon the corresponding portion of the inner surface dimensions and outer surface dimensions of the cosmetic cover as calculated above.

Accordingly, it is an object of the present invention to provide a system and method that precisely represents the prosthetic socket, limb, endoskeletal components and the alignment of these items with respect to each other, such that a cosmetic cover can be accurately milled based upon these characteristics; it is an object of the present invention to substantially automate the fabrication process of the cosmetic covers; it is an object of the present invention to provide a cosmetic cover system comprising at least two pieces that are separable from each other such that access to the endoskeletal components of the prosthetic limb is simplified and minimizes damage to the cosmetic cover; and it is an object of the present invention to provide a CAD/CAM system to preform the designing and data gathering steps. These and other objects of the present invention will be apparent from the following description, the attached drawings and the appended claims.

DETAILED DESCRIPTION

Figure 1:
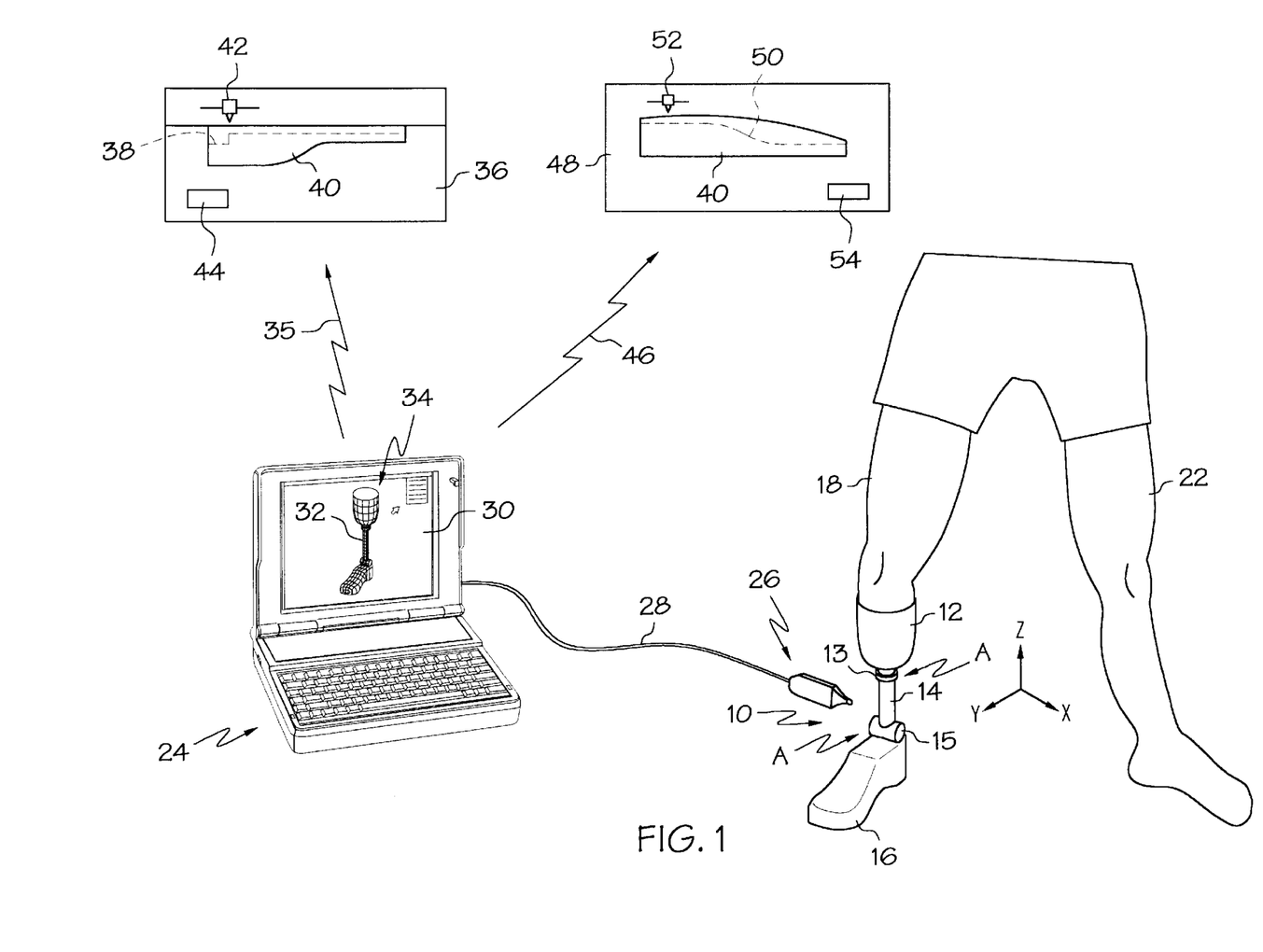
FIG. 1 is a block diagram representation of the system for performing the method of the present invention for a below-the-knee prosthetic limb.

As shown in FIG. 1, a typical below-the-knee ("BK") prosthetic limb 10 will include a hard plastic, custom fitted, socket component 12; a pylon assembly 14 coupled to the distal end of the socket component by interconnection components 13; and an ankle and foot assembly 16 coupled to the distal end of the pylon assembly 14 by interconnection components 15. The socket 12 is preferably precisely shaped to receive and provide comfort to the patient's residual limb 18. A system and method for designing and fabricating such a socket component is described in U.S. patent application Ser. No. 08/791,934, filed Jan. 31, 1997 now U.S. Pat. No. 5,824,111

Figure 2:
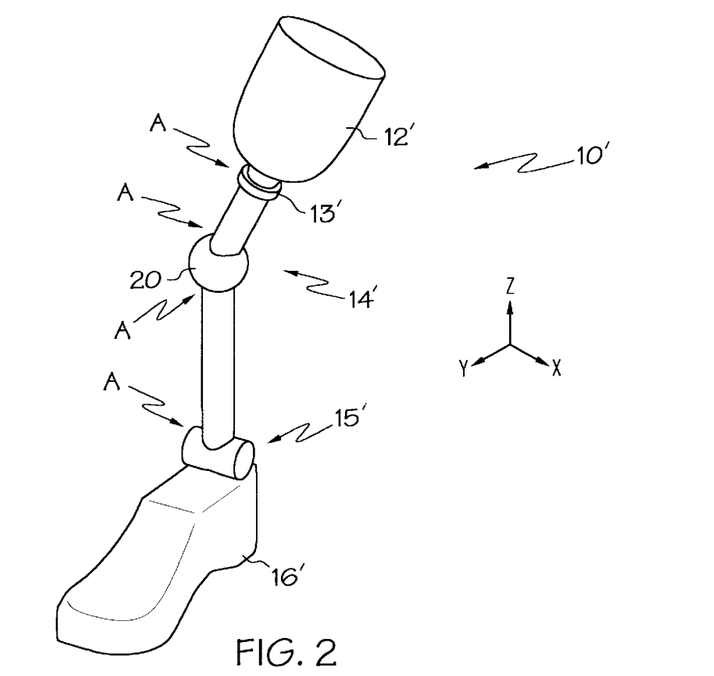
FIG. 2 is a diagram representation of an above-the-knee prosthetic limb.

As shown in FIG. 2, a typical above the knee prosthetic limb assembly ("AK") 10' will consist of a socket 12' adapted to engage the patient's residual limb; an upright assembly 14' coupled to the distal end of the socket 12' by interconnection components 13'; and a foot and ankle component 16' coupled to the distal end of the upright assembly 14' by interconnection components 15'. In an AK prosthetic limb assembly, the upright assembly 14' will also include a knee joint component 20.

Once the initial prosthetic limb 10 or 10' has been assembled, the patient, in the presence of a technician, will stand on the prosthesis and walk about. Initially, the particular socket and endoskeletal components (i.e., the upright assembly and the foot/ankle components) of the prosthetic limb will be somewhat out of alignment with each other, requiring adjustments such as height adjustments, toe in-toe out adjustments, alignment adjustments, etc. Once such conditions are determined, the technician will align and adjust the various endoskeletal components with respect to each other and with respect to the socket. Examples of the various alignment points are depicted in FIGS. 1 and 2 as "A". Such alignments, referring to the coordinate systems depicted in FIGS. 1 and 2, can be angular (XZ, YZ), rotational (about Z), translational (X, Y), length (Z), etc.

Once the prosthetic limb 10, 10' has been successfully fit and aligned with respect to the patient's particular physical characteristics, an outer cosmetic cover will then be fabricated. Preferably, the outer cosmetic cover will be used to cover the socket and endoskeletal components of the prosthetic limb and simulate the appearance of the sound limb 22, which is the limb opposing the amputated or residual limb 18.

The procedure for fabricating the cosmetic cover is performed using a computer-aided-design tool (CAD) 24, which also preferably includes a digitizing tool 26, built-in. Such a CAD/digitizing design tool is commercially available as the TracerCAD system, sold by Tracer Corp. of Miami, Fla. The digitizing tool 26 is preferably a wand-based digitizer that is able to gather surface, positional, orientational, angular and other dimensions from a positive physical representation of the patient's residual limb, the patient's sound limb, or the prosthetic limb components. This data is transmitted to the CAD tool 24 by a data-link or cord 28.

As described in U.S. patent application Ser. No. 08/791, 934, filed Jan. 31, 1997 now U.S. Pat. No. 5,824,111: the CAD tool preferably contains a software package to calculate the dimensions of a positive mold of the socket component 12, 12'; once calculated, the socket mold dimensions are downloaded to a milling machine (not shown), which mills the positive mold from a carving blank; and once milled, the positive mold is used to fabricated the socket from a thermoplastic preform cone (not shown) using a "Socket Manufacturing Unit" (not shown).

After the prosthetic limb 10, 10' is assembled, fitted and aligned as discussed above, the technician will preferably select the dimensions of the endoskeletal components (such as the upright assembly 14, 14' and the foot and ankle components 16, 16'), any interconnection components 13, 15, 13', 15', and any other components used to fabricate the prosthetic limb, from an internal memory (described below) in the CAD tool. As shown in FIG. 1, preferably the dimensions are accessible through a pull-down type menu 30. Accordingly, because the CAD tool will already be able to create a digital representation of the socket 32, the CAD tool will be able to create a digital representation of the entire assembled prosthetic limb 34 by including the remaining prosthetic limb components (i.e., the endoskeletal components) selected by the technician using the pull-down menu 30.

Based upon the entire combination of dimensions of these components, the CAD tool will be able to determine inner surface dimensions of a cosmetic cover to be worn over these components. But prior to determining these inner surface dimensions, the precise orientational and positional dimension of the various components with respect to one another must also be determined, so that the inner surface of the cosmetic cover can reflect such orienational and positional data. And in turn, so that the cosmetic cover will properly fit to the aligned and fitted prosthetic limb.

Accordingly, the digitizing tool 26 is next utilized to gather orientational and positional data at the various alignment points A. This orientational and positional data is transmitted to the CAD tool 24 over the data link 28. Using this orientational and positional data, in combination with the dimensions of the prosthetic limb components, the CAD tool 24 is able to calculate the precise inner surface dimensions for a cosmetic cover to be worn over the fitted and aligned prosthetic limb 10, 10'. These inner surface dimensions, once calculated, are transmitted over a data link 35 to a milling machine 36, adapted to carve the inner surface 38 of the cosmetic cover from a cover blank 40. The milling machine 36 includes a carving tool 42 controlled by a processing unit 44 having access to the downloaded inner surface dimensions. An example milling machine adequate for milling the inner surface 38 of the cosmetic cover from a cover blank 40 is a CARVER I or CARVER II CNC machine, commercially available from Benz Group Ltd, Horns Cross, Greenhithe, Kent U.K.

Preferably, before the inner surface 38 is carved, the digitizing tool 26 is used to gather the surface dimensions of the sound-side limb 22. Using these sound-side dimensions, the CAD tool 24 is able to calculate the precise outer surface dimensions for the cosmetic cover to be worn over the fitted and aligned prosthetic limb 10, 10'. These outer surface dimensions, once calculated, are transmitted over a data link 46 to a milling machine 48, adapted to carve the outer surface 50 of the cosmetic cover from the cover blank 40. The milling machine 48 includes a carving tool 52 controlled by a processing unit 54 having access to the inner surface dimensions. The milling machine 48 can be a separate milling machine or can be the same milling machine 36 used to carve the inner surface of the cosmetic cover. Preferably, both the inner surface and outer surface dimensions are downloaded to a single milling machine. And as will be described below, the milling machine separately carves two mating longitudinal halves of the cosmetic cover from two separate cover blanks. Furthermore, the milling machine preferably covers the inner surfaces and outer surfaces of the cosmetic cover in the same operation.

If a sound-limb is not available, the outer surface dimensions may be determined based upon a desirable limb template having adjustable circumferential values to match dimensions of the residual limb(s).

Figure 3:
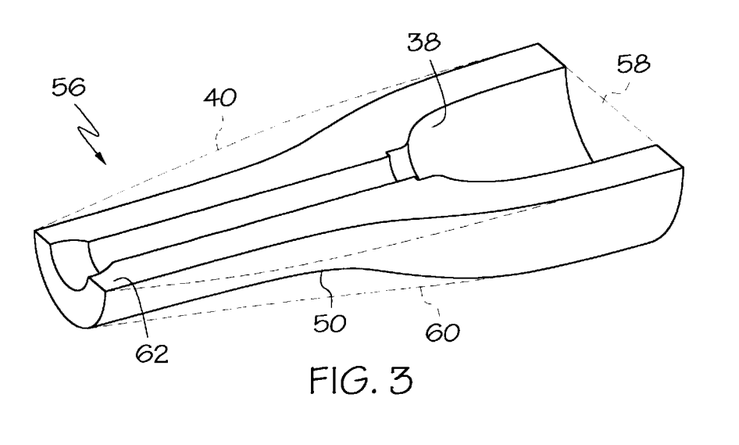
FIG. 3 is a perspective view of a cosmetic cover half, fabricated from a cast shown in broken lines, according to the present invention.
Figure 4:
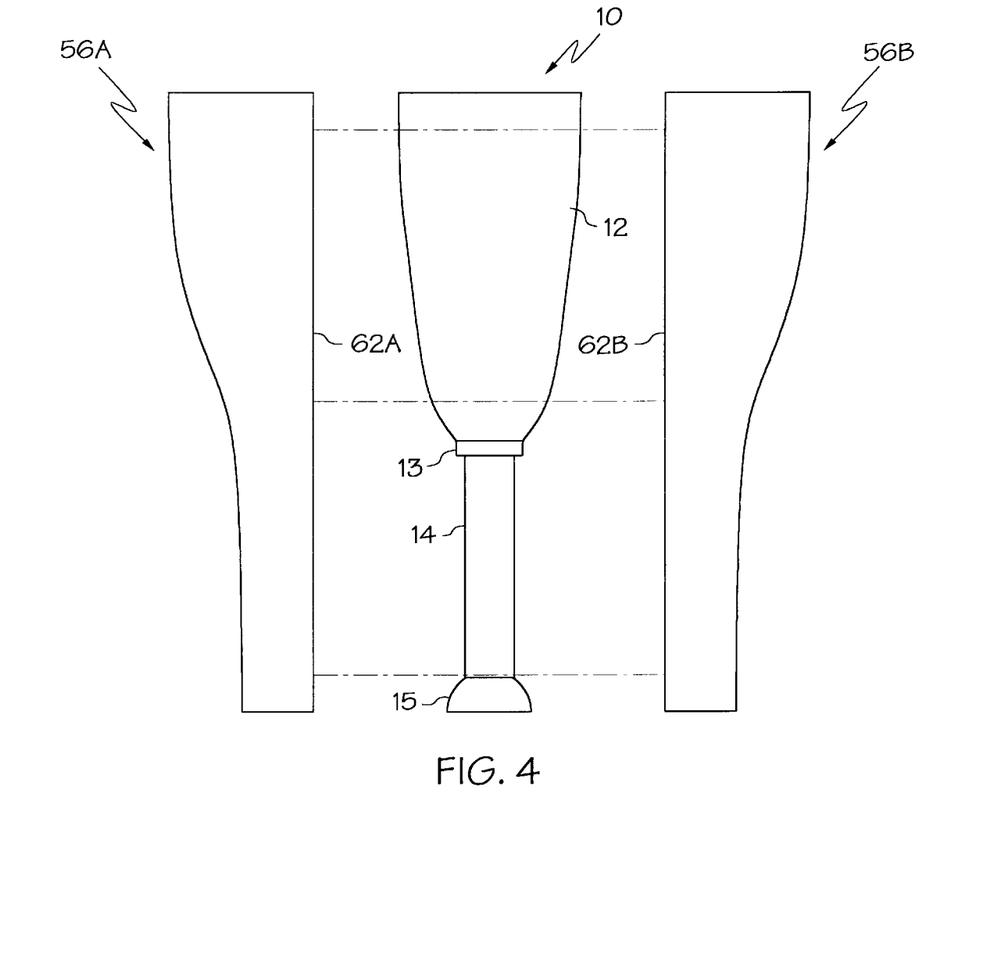
FIG. 4 is a perspective view of a pair of cosmetic cover halves mating about a prosthetic limb assembly according to the present invention.

As shown in FIGS. 3 and 4, the cosmetic cover 56 preferably includes two longitudinal halves 56a and 56b, which are each carved out of separate carving blanks 40 having a substantially flat interior surface 58 and a substantially dome-shaped exterior surface 60. The inner surface of the cosmetic cover 38 is carved into the inner surface 58 of the cover blank 40 and the outer surface 50 of the cosmetic cover is carved from the outer dome-shaped surface 60 of the carving blank 40.

As shown in FIG. 4, the inner surface 62a of the first cosmetic cover halve 56a is adapted to mate with inner surface 62b of the second cosmetic cover halve 56b and be coupled thereto using any conventional means for permanently or temporarily coupling such components together, such as adhesives, mechanical fasteners or the like.

Figure 7:
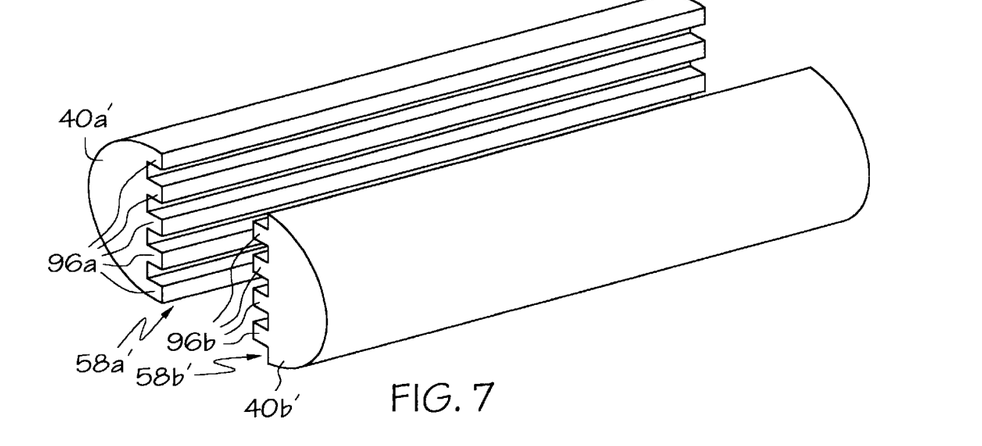
FIG. 7 is a perspective view of an embodiment of a pair of cosmetic cover half blanks for use with the present invention.

As shown in FIG. 7, in an alternate embodiment of the cover blanks 40' the interior surfaces 58a', 58b' of each cover blank 40a', 40b' include a plurality of teeth 96a, 96b extending along the length of the interior surface; where the teeth 96a of one cover blank are aligned to mesh with and engage the teeth 96b of the opposing cover blank. Thus, when the inner surface of the cosmetic cover is carved into the blanks 40a', 40b' as described above, a sufficient portion of the interlocking teeth 96a, 96b will remain such that when the two finished cover halves are subsequently mated, the two halves will mechanically interlock. A bonding agent may then be optionally applied between the finished cover halves when completed.

Figure 8:
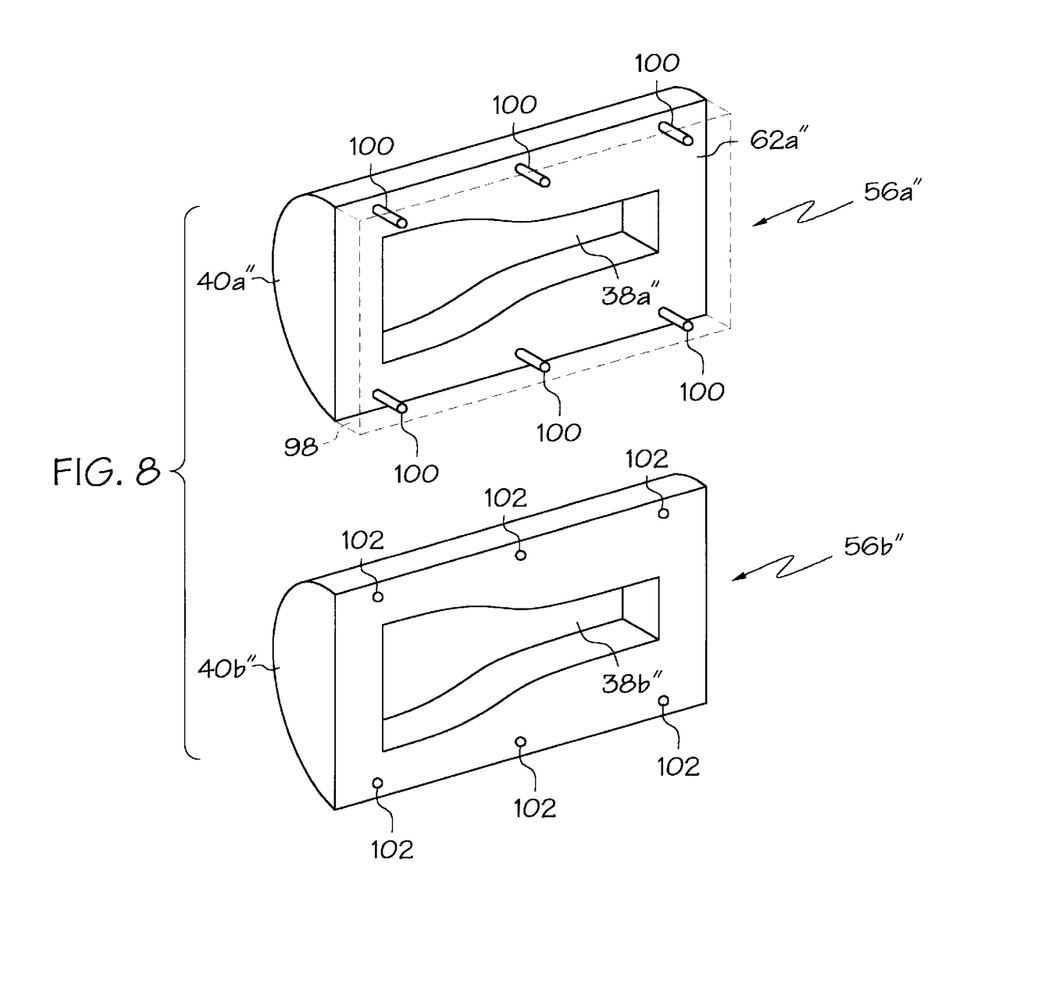
FIG. 8 is a perspective view of another embodiment of a pair of cosmetic cover half blanks, of which the inner surfaces have been milled according to one aspect of the present invention.

As shown in FIG. 8, in another alternate embodiment of the cover blanks, one of the cover blanks 40a" include an extended interior portion 98. The other one of the cover blanks 40b" may or may not have such an extended interior portion. Thus, when milling the interior surface 38a", the milling machine is adapted to carve away the entire extended interior portion 98 from the cover blank 40a", except for a plurality of pins 100 which extend outwardly from the flat interior surface 62a" of the finished cosmetic cover half 56a". The milling machine is also adapted to bore oppositely opposed bores 102 into the other carving blank 40b", when milling the interior surface 38b", such that the pins 100 will be received therein when the two halves of the cosmetic cover 56a", 56b" are mated. The locations of the pins 100 and bores 102 are determined according to the calculated inner and outer surface dimensions. A bonding agent may be optionally applied between the finished cover halves 56a", 56b" when completed.

Accordingly, because cosmetic cover 56 is preferably separated into two halves as described above, the inner surface 38 and outer surface 50 of the cosmetic cover halves can be easily milled using conventional milling machines, and when combined into a single cosmetic cover, the two halves can be easily separated from each other, providing easy access to the prosthetic limb components without damaging the cosmetic cover 56. And once all the necessary adjustments to the socket or endoskeletal components have been made, the cosmetic cover halves can be permanently bonded to each other over the socket and endoskeletal components.

Figure 5:
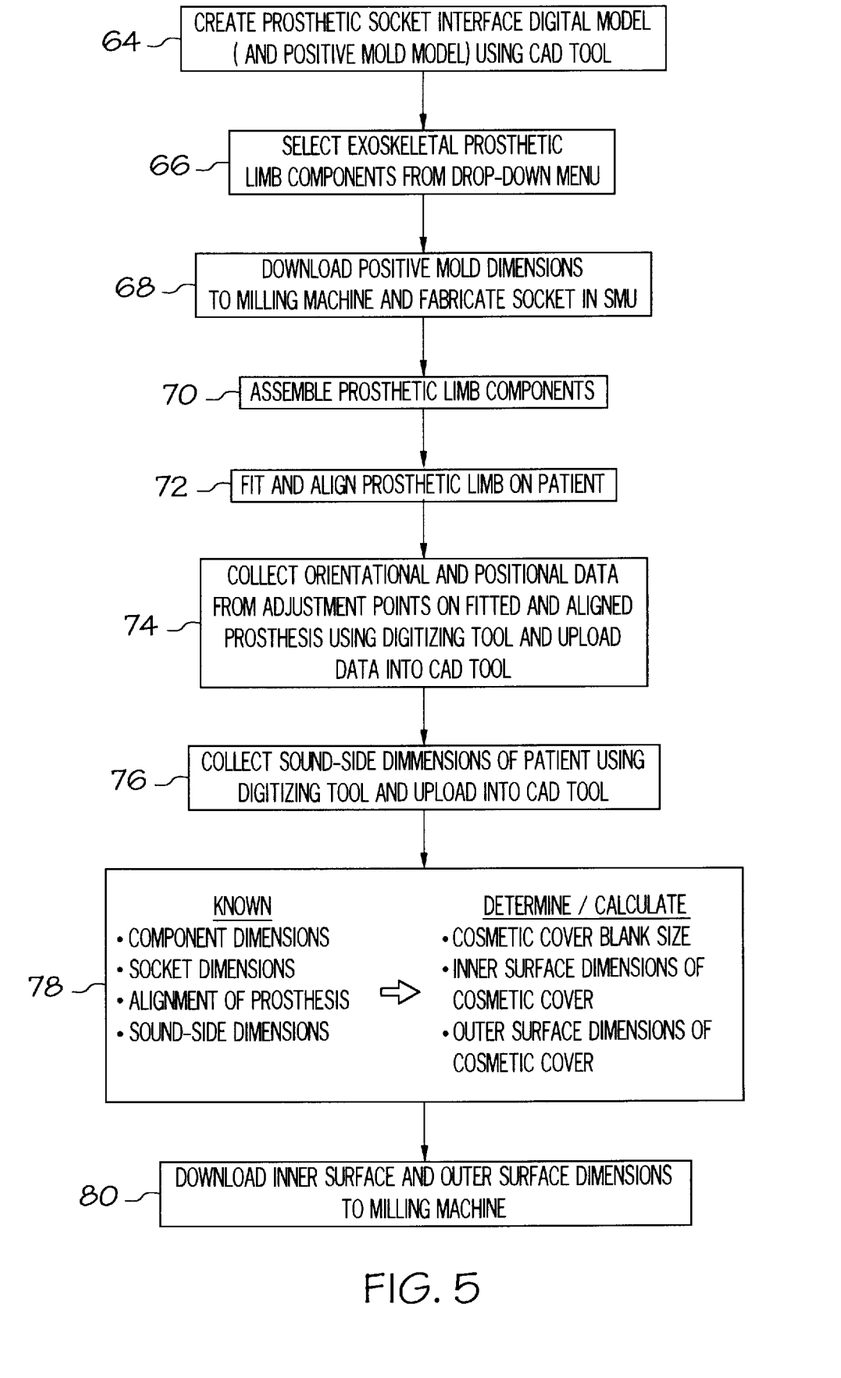
FIG. 5 is a flow-chart representation of a method according to the present invention.

The procedure for fabricating the cosmetic cover is shown in FIG. 5. In block 64 the digital model of the prosthetic limb socket 12 is first created using the CAD tool 24. In block 66, the desired prosthetic limb components to be assembled with the socket are selected using a pull-down menu on the CAD tool 24. In block 68, the positive mold dimensions for the socket are downloaded to a milling machine to mill the positive mold, and the socket is created in the SMU from a preform cone. In block 70, the socket is assembled with the prosthetic limb components. In block 72, the prosthetic limb components are adjusted and aligned with respect to each other. In block 74, the digitizing tool 26 is utilized to collect the orientational and positional data from the adjustment points A on the fitted and aligned prosthesis, and this data is then uploaded into the CAD tool 24. In block 76, the sound side dimensions of the patient are collected utilizing the digitizing tool 26 and these dimensions are uploaded to the CAD system 24. In block 78, the CAD tool is able to determine and calculate the cosmetic cover blank size, the inner surface dimensions of the cosmetic cover, and the outer surface dimensions of the cosmetic cover utilizing the known current component dimensions, socket dimensions, alignment characteristics of the prosthesis, alignment data of the prosthesis and the sound side dimensions. Finally, in block 80, the inner surface dimensions and outer surface dimensions are downloaded to the milling machine(s) to mill the cosmetic cover from the cover blanks 40.

Figure 6:
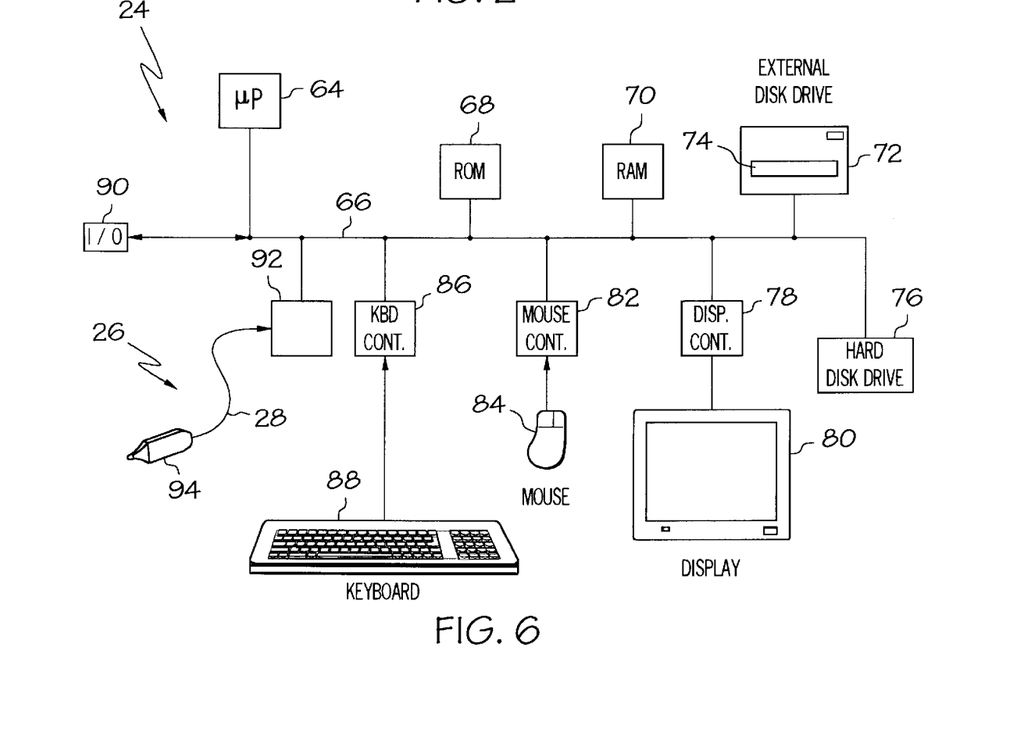
FIG. 6 is a schematic block-diagram representation of the CAD/digitizing system for use with the present invention.

As shown in FIG. 6, the above calculations for determining the dimensions of the inner surface 38 and outer surface 50 of the cosmetic cover 56 are preferably performed by the CAD system 24. The CAD system for use with the present invention can include a microprocessor 64 communicating over a communications bus 66 with an internal read only memory ("ROM") 68; an internal random-access memory ("RAM") 70; at least one external disk drive 72 adapted to read and/or write to an external memory device 74 such as a floppy disk, CD, etc., a hard disk 76; a display controller 78 for operating a display 80; a mouse controller 82 for operating a mouse device (a cursor control device such as a mouse, track ball, etc.) 84; a keyboard controller 86 for interfacing a keyboard 88; and at least one input/output interface (such as a modem device, a network device, a serial port, etc.) 90 for interfacing with other computers, memory devices, the milling machines, etc. The digitizing tool 26, including a controller 92 and a digitizing wand 94 communicating to each other via the data link 28, is preferably integrated into the CAD system 24 and communicates with the microprocessor 64 over the communication bus 66.

To perform the above calculations, a program, such as a software program, configured to perform these calculations is stored either in the ROM 68, the RAM 66, the external memory device 74, the hard disk 76 or is accessible by the microprocessor 64 via an IO interface 90. When the microprocessor 64 is executing the program, the microprocessor 64 will have access to the dimensions of the particular components of the prosthetic limb, the dimensions of the socket, the particular positional and orientational alignment point data, and the dimensions of the sound side limb of the patient. These dimensions (and data) can be stored in any representation, including a digital three-dimensional representation of any of the above components. Such dimensions can also be contained on any of the above memory devices, accessible through the IO interface 90, or can be simply typed in by the operator over the keyboard 88. Once the dimensions of the inner surface 38 and outer surface 50 of the cosmetic cover have been calculated, the microprocessor 64 then preferably downloads these dimensions over the datalinks 35, 46 to the milling machines 36, 48 such that the cosmetic cover can be fabricated as discussed above. It should be apparent to one of ordinary skill in the art, that is within the scope of the invention to perform some of the above steps manually or semi-manually (for example, downloading dimension from the CAD tool to the milling machine by copying the dimensions to a floppy disk and inserting the floppy disk into a disk-drive incorporated into the milling).

Therefore, having described the invention in detail and by reference to the drawings, it will be apparent that other modifications and variations are possible without departing from the scope of the invention as defined in the following claims.

What is claimed is:

1. A method for fabricating a cosmetic cover for a prosthetic limb, the prosthetic limb having a plurality of components including a socket for engaging a wearer's residual limb, an upright assembly coupled to a distal end of the socket, and a foot component coupled to a distal end of the upright assembly, the prosthetic limb also having a plurality of adjustment points for adjusting certain prosthetic limb components with respect to each other, the method comprising the steps of:

fitting and aligning the prosthetic limb to a wearer's residual limb;

collecting orientational and positional data from at least one of the adjustment points;

sending the orientational and positional data to a computer-aided design tool, the computer-aided design tool having access to component dimensions, the component dimensions include the dimensions of at least the socket and the upright assembly;

calculating inner surface dimensions for a cosmetic cover to be worn over the prosthetic limb according to the component dimensions and the orientational and positional data; and downloading the inner surface dimensions to a computer controlled milling machine, the milling machine being adapted to carve the inner surface of the cosmetic cover from a carving blank using the inner surface dimensions.

2. The method of claim 1, wherein a wearer has a sound limb and a corresponding residual limb, and the method further comprises sending sound-side dimensions of the sound limb to the computer-aided design tool;

calculating outer surface dimensions for the cosmetic cover to be worn over the prosthetic limb according to the sound-side dimensions; and downloading the outer surface dimensions to a computer controlled milling machine, the milling machine being adapted to carve the outer surface of the cosmetic cover from a carving blank using the outer surface dimensions.

3. The method of claim 2, further comprising the step of determining a carving blank size according to the sound-side dimensions.

4. The method of claim 2, wherein the sound-side dimensions are gathered using a computer-controlled digitizing tool.

5. The method of claim 4, wherein the computer-controlled digitizing tool is integrated with the computer-aided design tool.

6. The method of claim 1, wherein the collecting step is performed using a computer-controlled digitizing tool, capable of measuring spatial characteristics of a positive physical representation of the prosthetic limb.

7. The method of claim 6, wherein a wearer has a sound limb and a corresponding residual limb, and the method further comprises sending sound-side dimensions of the sound limb to the computer-aided design tool;

calculating outer surface dimensions for the cosmetic cover to be worn over the prosthetic limb according to the sound-side dimensions; and downloading the outer surface dimensions to a computer controlled milling machine, the milling machine being adapted to carve the outer surface of the cosmetic cover from a carving blank using the outer surface dimensions.

8. The method of claim 7, wherein the method further includes the step of collecting the sound-side dimensions using the computer-controlled digitizing tool.

9. The method of claim 1, wherein the collecting step is performed while a wearer is wearing the fitted and aligned prosthetic limb.

10. The method of claim 1, wherein the computer-aided design tool includes a database for storing dimensions for a plurality of types or sizes of the components, and the method includes the steps of:

choosing desired components for constructing the prosthetic limb; and calculating the inner surface dimensions according to dimensions of the chosen components and the orientational and positional data.

11. The method of claim 10, wherein the choosing step is performed by the steps of:

activating an on-screen menu of the computer-aided design tool, the menu displaying names of components stored in the database; and selecting at least one of component from the menu.

12. The method of claim 1, wherein the orientational and positional data include angular, rotational and alignment characteristics of the components with respect to each other.

13. A method for fabricating a cosmetic cover for a prosthetic limb from a carving blank system having at least two mating longitudinal carving blanks, the prosthetic limb having a plurality of components including a socket for engaging a wearer's residual limb, an upright assembly coupled to a distal end of the socket, and a foot component coupled to a distal end of the upright assembly, the prosthetic limb also having a plurality of adjustment points for adjusting certain prosthetic limb components with respect to each other, the method comprising the steps of:

fitting and aligning the prosthetic limb to a wearer's residual limb;

collecting orientational and positional data from at least one of the adjustment points;

sending the orientational and positional data to a computer-aided design tool, the computer-aided design tool having access to component dimensions, the component dimensions include the dimensions of at least the socket and the upright assembly;

calculating inner surface dimensions for a cosmetic cover to be worn over the prosthetic limb according to the component dimensions and the orientational and positional data;

carving an inner surface of one of the carving blanks according to a longitudinal portion of the inner surface dimensions; and carving an inner surface of another one of the carving blanks according to another longitudinal portion of the inner surface dimensions.

14. The method of claim 13, wherein a wearer has a sound limb and a corresponding residual limb, and the method further comprises:

sending sound-side dimensions of the sound limb to the computer-aided design tool;

calculating outer surface dimensions for the cosmetic cover to be worn over the prosthetic limb according to the sound-side dimensions;

carving an outer surface of one of the carving blanks according to a longitudinal portion of the outer surface dimensions; and carving an outer surface of another one of the carving blanks according to another longitudinal portion of the outer surface dimensions.

15. A computerized tool for designing a cosmetic cover for a prosthetic limb comprising:

means for storing or accessing prosthetic limb component dimensions, the prosthetic limb component dimensions including at least dimensions of a socket for engaging a wearer's residual limb and dimensions of an upright assembly for coupling to a distal end of the socket;

means for collecting or accessing orientational and positional data of prosthetic limb components from a fitted and aligned prosthetic limb;

a memory containing a software program for calculating inner surface dimensions for a cosmetic cover to be worn over the fitted and aligned prosthetic limb based upon the prosthetic limb component dimensions and the orientational and positional data; and a processing circuit, having access to the prosthetic limb component dimensions and the orientational and positional data, for executing the software program.

16. The computerized tool of claim 15, wherein a wearer has a sound limb and a corresponding residual limb, and the computerized tool further comprises:

means for accessing sound-side dimensions of the sound limb; and a memory containing a software program for calculating outer surface dimensions for the cosmetic cover based upon the sound-side dimensions.

17. The computerized tool of claim 16, further comprising a digitizing tool for gathering the sound-side dimensions.

18. The computerized tool of claim 15, further comprising a digitizing tool for gathering the orientational and positional data.

19. The computerized tool of claim 15, further comprising:

a memory for storing a database containing dimensions of a plurality of types or sizes of components; and a memory containing a software program for generating an on-screen, graphical, menu-based interface that allows a user to select particular dimensions from the database;

wherein the processing circuit executes the software program to calculate inner surface dimensions for a cosmetic cover to be worn over the fitted and aligned prosthetic limb based upon selected prosthetic limb component dimensions and the orientational and positional data.

20. A method for fabricating a cosmetic cover for a prosthetic limb comprising the steps of:

positioning a first longitudinal carving blank in a milling machine;

carving an indentation into a first longitudinal surface of the first carving blank sufficient to receive a first portion of the prosthetic limb, using the milling machine;

carving an outer surface of the first carving blank, substantially opposing the first longitudinal surface of the first carving blank, to simulate the appearance of a first portion of a sound limb, using the milling machine;

positioning a second longitudinal carving blank in the milling machine;

carving an indentation into a first longitudinal surface of the second carving blank sufficient to receive a second portion of the prosthetic limb, using the milling machine; and carving an outer surface of the second carving blank, substantially opposing the first longitudinal surface of the second carving blank, to simulate the appearance of a second portion of a sound limb; the first longitudinal surface of the first carving blank being adapted to mate with the first longitudinal surface of the second carving blank.

* * * * *